United States Patent [19]

Edouard

[11] Patent Number: 4,717,772

[45] Date of Patent: Jan. 5, 1988

[54] ALKYL ZIRCONATE COLOR IMPROVEMENT

[75] Inventor: Fritzbert Edouard, Spring Valley, N.Y.

[73] Assignee: Stauffer Chemical Company, Westport, Conn.

[21] Appl. No.: 15,760

[22] Filed: Feb. 17, 1987

[51] Int. Cl.$^4$ .............................................. C07F 7/00
[52] U.S. Cl. ...................................................... 556/54
[58] Field of Search .......................................... 556/54

[56] References Cited

U.S. PATENT DOCUMENTS

| 2,720,504 | 10/1955 | Caldwell et al. | 556/54 X |
| 2,977,378 | 3/1961 | Kasper | 556/54 X |
| 3,754,011 | 3/1973 | Hoch | 556/54 X |

*Primary Examiner*—Paul F. Shaver
*Attorney, Agent, or Firm*—Richard P. Fennelly

[57] ABSTRACT

The color of alkyl zirconate compounds that have become discolored is improved by treating the zirconate with a nitrogen oxide oxidant, such as nitric acid, to achieve the desired color improvement.

10 Claims, No Drawings

ALKYL ZIRCONATE COLOR IMPROVEMENT

BACKGROUND OF THE INVENTION

1. Field of the Invention

The present invention relates to the color improvement of alkyl zirconates.

2. Description of the Prior Art

In U.S. Pat. No. 4,452,724 to G. C. Ciomo, a process for the color improvement of alkyl vanadate compounds by the use of a nitrogen oxide oxidant is described. The description contained in that patent regarding the type of compounds which could be treated by such a procedure is limited to vanadate species.

SUMMARY OF THE PRESENT INVENTION

The present invention is a process for the color improvement of alkyl zirconate compounds which have become decolorized, e.g., by becoming at least partially decomposed. It comprises treating the alkyl zirconate with a nitrogen oxide oxidant to achieve the color improvement.

DETAILED DESCRIPTION OF THE PRESENT INVENTION

The terminology "alkyl zirconate" is intended to cover zirconium alkoxides such as those manufactured from solid zirconium tetrachloride and the respective alcohol in the presence of a suitable catalyst such as ammonia. Representative compounds within this class include zirconium tetra-n-propylate, and zirconium tetra-n-butylate.

Alkyl zirconates, such as those described before, which have become discolored, e.g., due to chemical decomposition, can have their color improved by treatment with a nitrogen oxide oxidant under conditions which result in such color improvement.

Various substances can be used to supply the nitrogen oxide oxidant to the discolored or darkened alkyl zirconate. For example, nitric acid can be used. Alternatively, a nitrogen oxide gas, such as nitrogen dioxide, can be employed.

The amount of nitrogen oxide oxidant-containing substance which can be employed in accordance with the present invention to achieve the desired color improvement can be quite small in comparison to the amount of zirconate. Generally, amounts of from about 0.01% to about 2%, by weight of the zirconate, would be sufficient. The contacting of the zirconate and the nitrogen oxide oxidant can be conducted at temperatures ranging from about room temperature (about 20° C.) up to about 100° F., if desired. In the case of nitric acid as the nitrogen oxide oxidant, the acid can be added to the zirconate and allowed to stand, after agitation, for a sufficient amount of time (e.g., for several days) until the desired level of color improvement is obtained.

This invention is further illustrated by the Example which follows.

EXAMPLE 1

Reagent grade nitric acid (1-2 mls) was added to about 4 ounces of 75 weight percent tetra n-propylzirconate in normal octane. The Gardner color reading of the zirconate before addition of the nitric acid was 12. The zirconate and nitric acid were placed in a nitrogen padded 8-ounce bottle which was sealed, shaken well for about 1 minute, and let stand over a weekend. The temperature in the vicinity of the bottle was about 90° F. After being allowed to stand, the sample improved in color to a Gardner reading of 9.

The foregoing example illustrates certain preferred embodiments of the present invention and should not be construed in a limiting sense. The scope of protection that is sought is set forth in the claims which follow.

I claim:

1. A process for the color improvement of alkyl zirconates which comprises treating the alkyl zirconate with an effective amount of a nitrogen oxide oxidant to achieve the color improvement.

2. A process as claimed in claim 1 wherein the zirconate is treated with nitric acid.

3. A process as claimed in claim 1 wherein the zirconate is treated with a nitrogen oxide oxidant-containing gas.

4. A process as claimed in claim 1 wherein the zirconate is treated with nitrogen dioxide.

5. A process as claimed in claim 1 wherein the zirconate is treated with nitric oxide.

6. A process as claimed in claim 1 wherein the zirconate is treated with from about 0.1% to about 2%, by weight, of a substance containing the nitrogen oxide oxidant.

7. A process as claimed in claim 1 wherein the treatment takes place at a temperature of from about 20° C. to about 100° F.

8. A process as claimed in claim 1 wherein the zirconate is treated with from about 0.1% to about 2%, by weight, of a substance containing the nitrogen oxide oxidant at a temperature of from about 20° C. to about 100° F.

9. A process as claimed in claim 4 wherein the zirconate is treated with from about 0.1% to about 2%, by weight, of nitric acid.

10. A process as claimed in claim 9 wherein the treatment takes place at a temperature of from about 20° C. to about 100° F.

* * * * *